United States Patent
Bratcher et al.

(10) Patent No.: US 11,963,965 B2
(45) Date of Patent: Apr. 23, 2024

(54) METHODS OF TREATING CYSTIC FIBROSIS TRANSMEMBRANE CONDUCTANCE REGULATOR (CFTR) DYSFUNCTION

(71) Applicant: National Jewish Health, Denver, CO (US)

(72) Inventors: Preston E. Bratcher, Arvada, CO (US); Pamela L. Zeitlin, Denver, CO (US)

(73) Assignee: National Jewish Health, Denver, CO (US)

( * ) Notice: Subject to any disclaimer, the term of this patent is extended or adjusted under 35 U.S.C. 154(b) by 264 days.

(21) Appl. No.: 17/130,580

(22) Filed: Dec. 22, 2020

(65) Prior Publication Data

US 2021/0196728 A1 Jul. 1, 2021

Related U.S. Application Data

(60) Provisional application No. 62/953,877, filed on Dec. 26, 2019.

(51) Int. Cl.
| | |
|---|---|
| *A61K 31/558* | (2006.01) |
| *A61K 31/352* | (2006.01) |
| *A61K 31/404* | (2006.01) |
| *A61K 31/4155* | (2006.01) |
| *A61K 31/443* | (2006.01) |
| *A61K 31/4439* | (2006.01) |
| *A61K 31/47* | (2006.01) |
| *A61K 31/502* | (2006.01) |
| *A61K 45/06* | (2006.01) |
| *A61P 11/00* | (2006.01) |

(52) U.S. Cl.
CPC .......... *A61K 31/558* (2013.01); *A61K 31/352* (2013.01); *A61K 31/404* (2013.01); *A61K 31/4155* (2013.01); *A61K 31/443* (2013.01); *A61K 31/4439* (2013.01); *A61K 31/47* (2013.01); *A61K 31/502* (2013.01); *A61K 45/06* (2013.01); *A61P 11/00* (2018.01)

(58) Field of Classification Search
CPC ..................................................... A61P 11/00
See application file for complete search history.

(56) References Cited

U.S. PATENT DOCUMENTS

2018/0055873 A1 3/2018 Dessen et al.

FOREIGN PATENT DOCUMENTS

WO WO 2009/132271 10/2009

OTHER PUBLICATIONS

De Lisle et al., Lubiprostone ameliorates the cystic fibrosis mouse intestinal phenotype, BMC Gastroenterology, 2010, 10:107, pp. 1-12 (Year: 2010).*
Wainwright et al., Lumacaftor-Ivacaftor in Patients with Cystic Fibrosis Homozygous for Phe508del CFTR, The New England Journal of Medicine, 2015, 375:3, pp. 220-231 (Year: 2015).*

(Continued)

*Primary Examiner* — Clinton A Brooks
*Assistant Examiner* — Andrew P Lee
(74) *Attorney, Agent, or Firm* — Sheridan Ross P.C.

(57) ABSTRACT

Methods of treating cystic fibrosis transmembrane conductance regulator (CFTR)-mediated disease, such as cystic fibrosis, in patients with residual function mutations.

22 Claims, 7 Drawing Sheets

Specification includes a Sequence Listing.

(56) References Cited

OTHER PUBLICATIONS

Boyle et al. "A CFTR corrector (lumacaftor) and CFTR potentiator ivacaftor) for treatment of patients with cystic fibrosis who have a phe508del CFTR mutation: a phase 2 randomised controlled trial," The Lancet Respiratory Medicine, Jul. 2014, vol. 2, No. 7, pp. 527-538.
Colombo "Cystic fibrosis transmembrane conductance-regulator modulators for children," The Lancet Respiratory Medicine, Jul. 2017, vol. 5, No. 7, pp. 536-537.
Davis "Another Beginning for Cystic Fibrosis Therapy," The New England Journal of Medicine, Jul. 2015, vol. 373, No. 3, pp. 274-276.
Eckford et al. "VX-809 and Related Corrector Compounds Exhibit Secondary Activity Stabilizing Active F508del-CFTR after Its Partial Rescue to the Cell Surface," Chemistry & Biology, May 2014, vol. 21, pp. 666-678.
Elborn et al. "Efficacy and safety of lumacaftor/ivacaftor combination therapy in patients with cystic fibrosis homozygous for Phe508del CFTR by pulmonary function subgroup," The Lancet Respiratory Medicine, Aug. 2016, vol. 4, No. 8, pp. 617-626.
Ratjen et al. "Efficacy and safety of lumacaftor and ivacaftor in patients aged 6-11 years with cystic fibrosis homozygous for F508del-CFTR: a randomised, placebo-controlled, phase 3 trial," The Lancet Respiratory Medicine, Jul. 2017, vol. 5, pp. 557-567.
Van Goor et al. "Correction of the F508del-CFTR protein processing defect in vitro by the investigational drug VX-809," PNAS, Nov. 15, 2011, vol. 108, No. 46, pp. 18843-18848.
Wainwright et al. "Lumacaftor-Ivacaftor in Patients with Cystic Fibrosis Homozygous for Phe508del CFTR," The New England Journal of Medicine, Jul. 2015, vol. 373, No. 3, pp. 220-231.
Wilson et al. "Lubiprostone in constipation: clinical evidence and place in therapy," Therapeutic Advances in Chronic Disease, 2015, vol. 6, No. 2, pp. 40-50.
Zhang et al. "Lumacaftor/ivacaftor combination for CF patients homozygous for Phe508del-CFTR," Drugs of Today, Apr. 2016, vol. 52, No. 4, pp. 229-237.
International Search Report and Written Opinion for International (PCT) Patent Application No. PCT/US20/66570, dated Mar. 25, 2021 16 pages.
International Preliminary Report on Patentability for International (PCT) Patent Application No. PCT/US2020/066570, dated Jul. 7, 2022 9 pages.
Grubb et al. "Pathophysiology of Gene-Targeted Mouse Models for Cystic Fibrosis," Physiological Reviews, Jan. 1999, vol. 79, Suppl. No. 1, pp. S193-S214.
O'Brien et al. "Lubiprostone for Constipation in Adults with Cystic Fibrosis: A Pilot Study," The Annals of Pharmacotherapy, Sep. 2011, vol. 45, pp. 1061-1066.
Ma et al. "High-affinity Activators of Cystic Fibrosis Transmembrane Conductance Regulator (CFTR) Chloride Conductance Identified by High-throughput Screening," The Journal of Biological Chemistry, Oct. 2002, vol. 277, No. 40, pp. 37235-37241.
Namkung et al. "Novel Amino-Carbonitrile-Pyrazole Identified in a Small Molecule Screen Activates Wild-Type and AF508 Cystic Fibrosis Transmembrane Conductance Regulator in the Absence of a CAMP Agonist," Molecular Pharmacology, Sep. 2013, vol. 84, No. 3, pp. 384-392.

\* cited by examiner

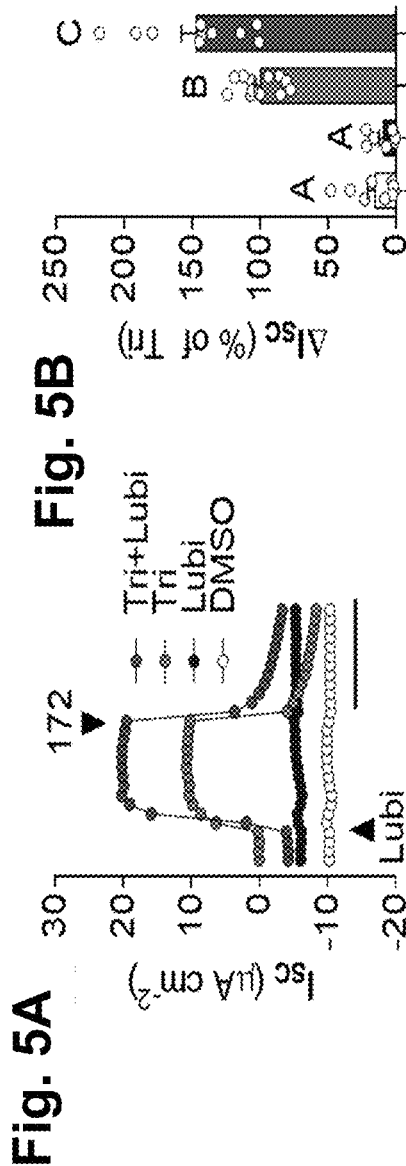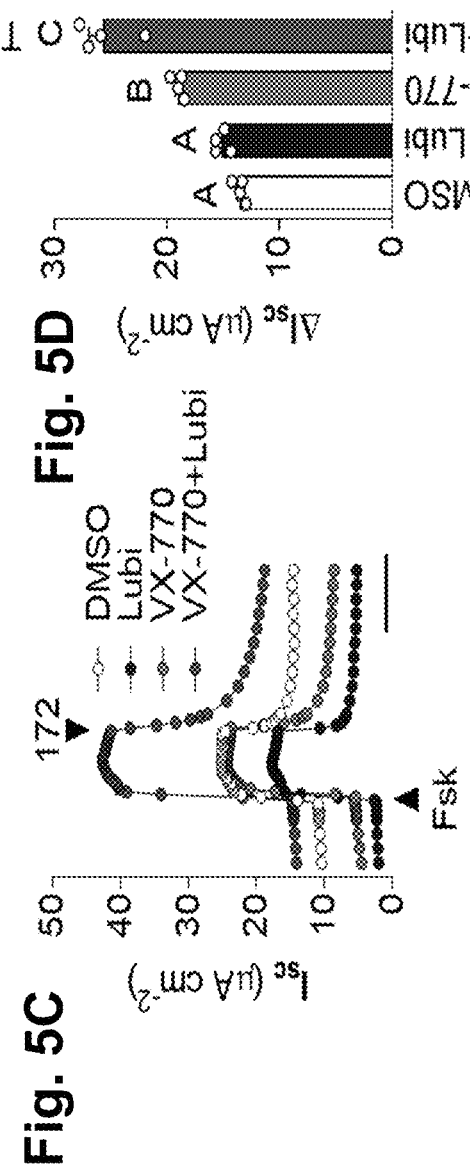

SEQUENCE LISTING

```
<160> NUMBER OF SEQ ID NOS: 1

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240
```

-continued

```
Gly Arg Met Met Met Lys Tyr Arg Asp Gln Arg Ala Gly Lys Ile Ser
                245                 250                 255
Glu Arg Leu Val Ile Thr Ser Glu Met Ile Glu Asn Ile Gln Ser Val
            260                 265                 270
Lys Ala Tyr Cys Trp Glu Ala Met Glu Lys Met Ile Glu Asn Leu
        275                 280                 285
Arg Gln Thr Glu Leu Lys Leu Thr Arg Lys Ala Ala Tyr Val Arg Tyr
    290                 295                 300
Phe Asn Ser Ser Ala Phe Phe Ser Gly Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
            340                 345                 350
Gln Phe Pro Trp Ala Val Gln Thr Trp Tyr Asp Ser Leu Gly Ala Ile
        355                 360                 365
Asn Lys Ile Gln Asp Phe Leu Gln Lys Gln Glu Tyr Lys Thr Leu Glu
    370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
            420                 425                 430
Phe Ser Leu Leu Gly Thr Pro Val Leu Lys Asp Ile Asn Phe Lys Ile
        435                 440                 445
Glu Arg Gly Gln Leu Leu Ala Val Ala Gly Ser Thr Gly Ala Gly Lys
    450                 455                 460
Thr Ser Leu Leu Met Val Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Ile Val Leu Gly Glu Gly
    530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
```

```
                660                 665                 670
Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
        690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080
```

```
Leu His Thr Ala Asn Trp Phe Leu Tyr Leu Ser Thr Leu Arg Trp
1085                1090                1095

Phe Gln Met Arg Ile Glu Met Ile Phe Val Ile Phe Phe Ile Ala
1100                1105                1110

Val Thr Phe Ile Ser Ile Leu Thr Thr Gly Glu Gly Glu Gly Arg
1115                1120                1125

Val Gly Ile Ile Leu Thr Leu Ala Met Asn Ile Met Ser Thr Leu
1130                1135                1140

Gln Trp Ala Val Asn Ser Ser Ile Asp Val Asp Ser Leu Met Arg
1145                1150                1155

Ser Val Ser Arg Val Phe Lys Phe Ile Asp Met Pro Thr Glu Gly
1160                1165                1170

Lys Pro Thr Lys Ser Thr Lys Pro Tyr Lys Asn Gly Gln Leu Ser
1175                1180                1185

Lys Val Met Ile Ile Glu Asn Ser His Val Lys Lys Asp Asp Ile
1190                1195                1200

Trp Pro Ser Gly Gly Gln Met Thr Val Lys Asp Leu Thr Ala Lys
1205                1210                1215

Tyr Thr Glu Gly Gly Asn Ala Ile Leu Glu Asn Ile Ser Phe Ser
1220                1225                1230

Ile Ser Pro Gly Gln Arg Val Gly Leu Leu Gly Arg Thr Gly Ser
1235                1240                1245

Gly Lys Ser Thr Leu Leu Ser Ala Phe Leu Arg Leu Leu Asn Thr
1250                1255                1260

Glu Gly Glu Ile Gln Ile Asp Gly Val Ser Trp Asp Ser Ile Thr
1265                1270                1275

Leu Gln Gln Trp Arg Lys Ala Phe Gly Val Ile Pro Gln Lys Val
1280                1285                1290

Phe Ile Phe Ser Gly Thr Phe Arg Lys Asn Leu Asp Pro Tyr Glu
1295                1300                1305

Gln Trp Ser Asp Gln Glu Ile Trp Lys Val Ala Asp Glu Val Gly
1310                1315                1320

Leu Arg Ser Val Ile Glu Gln Phe Pro Gly Lys Leu Asp Phe Val
1325                1330                1335

Leu Val Asp Gly Gly Cys Val Leu Ser His Gly His Lys Gln Leu
1340                1345                1350

Met Cys Leu Ala Arg Ser Val Leu Ser Lys Ala Lys Ile Leu Leu
1355                1360                1365

Leu Asp Glu Pro Ser Ala His Leu Asp Pro Val Thr Tyr Gln Ile
1370                1375                1380

Ile Arg Arg Thr Leu Lys Gln Ala Phe Ala Asp Cys Thr Val Ile
1385                1390                1395

Leu Cys Glu His Arg Ile Glu Ala Met Leu Glu Cys Gln Gln Phe
1400                1405                1410

Leu Val Ile Glu Glu Asn Lys Val Arg Gln Tyr Asp Ser Ile Gln
1415                1420                1425

Lys Leu Leu Asn Glu Arg Ser Leu Phe Arg Gln Ala Ile Ser Pro
1430                1435                1440

Ser Asp Arg Val Lys Leu Phe Pro His Arg Asn Ser Ser Lys Cys
1445                1450                1455
```

```
Lys Ser Lys Pro Gln Ile Ala  Ala Leu Lys Glu Glu  Thr Glu Glu
    1460            1465                1470

Glu Val  Gln Asp Thr Arg Leu
    1475             1480
```

METHODS OF TREATING CYSTIC FIBROSIS TRANSMEMBRANE CONDUCTANCE REGULATOR (CFTR) DYSFUNCTION

CROSS-REFERENCE TO RELATED APPLICATIONS

This application claims the benefit of priority under 35 U.S.C. § 119(e) to U.S. Provisional Patent Application No. 62/953,877, filed Dec. 26, 2019. The entire disclosure of U.S. Provisional Patent Application No. 62/953,877 is incorporated herein by reference.

REFERENCE TO SEQUENCE LISTING

This application contains a Sequence Listing submitted as an electronic text file named "2879-223_Sequence_Listing_ST25.txt", having a size in bytes of 13,000 bytes, and created on Dec. 22, 2020. The information contained in this electronic file is hereby incorporated by reference in its entirety pursuant to 37 CFR § 1.52(e)(5).

TECHNICAL FIELD

This invention relates generally to the field of treating cystic fibrosis in patients with residual function mutations using activators of Cystic Fibrosis Transmembrane Conductance Regulator (CFTR), their pharmaceutical compositions, and combinations of other CFTR modulating compounds.

BACKGROUND

Cystic fibrosis (CF) is a recessive genetic disease that affects approximately 70,000 children and adults worldwide. Despite progress in the treatment of CF, there is no cure. In patients with CF, mutations in CFTR endogenously expressed in respiratory epithelia lead to reduced apical anion secretion, causing an imbalance in ion and fluid transport. The resulting decrease in anion transport contributes to enhanced mucus accumulation in the lung and accompanying microbial infections that ultimately cause death in CF patients. In addition to respiratory disease, CF manifests itself in multiple body systems, including, but not limited to chronic obstructive pulmonary disease (COPD)-like disease, pancreatic exocrine deficiency, urogenital dysfunction, and abnormally high electrolyte concentration in the sweat of the cystic fibrosis patient. Clinical manifestations may include nasal polyps, bronchiectasis, bronchitis, pneumonia, respiratory failure, gall bladder disease, intussusception, meconium ileus, salt depletion, pancreatic exocrine deficiency causing intestinal malabsorption of fats, proteins, and to a lesser extent, carbohydrates, pancreatitis, peptic ulcers, rectal prolapse, diabetes, nutritional deficiencies, arthritis, vas deferens with consequent aspermia and absence of fructose in the ejaculate, failure to thrive, and delayed puberty. The cystic fibrosis patient faces a high risk of morbidity and mortality due to frequent pulmonary infection. CF patients typically suffer from pancreatic insufficiency that, if left untreated, result in death. In addition, the majority of males with cystic fibrosis are infertile, and fertility is reduced among females with cystic fibrosis.

The cystic fibrosis transmembrane conductance regulator (CFTR/ABCC7) is an ATP- and PKA-dependent chloride channel, regulating chloride and bicarbonate ion flux across apical membranes of polarized epithelial cells in tissues such as lung, gut, and pancreas. The tertiary structure of CFTR is arranged into two membrane-spanning domains with six transmembrane helices in each membrane-spanning domain, two intracellular nucleotide binding domains, and a regulatory domain. Mutations in the CFTR gene cause the autosomal-recessive genetic disease CF.

Sequence analysis of the CFTR gene (wild-type amino acid sequence of CFTR is represented herein by SEQ ID NO:1) has revealed a variety of disease-causing mutations. To date, greater than 2000 disease-causing mutations in the CF gene have been identified and about 242 of these mutations are known to cause CF. The most prevalent protein mutation is a deletion of phenylalanine at position 508 of the CFTR amino acid sequence (commonly referred to as F508del protein mutation). This mutation occurs in approximately 70% of the cases of CF and is associated with severe disease. Other commonly occurring mutations include A455E, G542X, G551D, N1303K, and R117H.

F508del alters the folding and thermostability and disrupts the intramolecular assembly of CFTR. These conformational defects lead to impaired trafficking of the protein and retention in the endoplasmic reticulum. The minute fraction of F508del-CFTR molecules that manage to reach the cell surface exhibit altered channel activity and reduced cell surface stability at physiological temperature. A pharmacological chaperone (VX-809 or lumacaftor) was found to be partially effective in rescuing the functional expression of F508del-CFTR to the cell surface in heterologous expression systems (Van Goor et al, 2011 PNAS 108:18843-48; Eckford et al, 2014 Chem Biol 21:666-78). Together with KALYDECO® (VX-770 or ivacaftor), a drug that enhances channel activity, lumacaftor significantly enhanced the functional activity of F508del-CFTR in pre-clinical studies of primary bronchial cell cultures and rectal biopsy-derived organoids (this combination therapy has recently been registered as ORKAMBI®). In clinical trials, this combination led to significant improvement in lung function with an approximately 3% increase in forced expiratory volume in 1-s (FEV1) for F508del homozygous patients (Boyle et al, 2014 Lancet Respir Med 2:527-38; Wainwright et al, 2015 N Engl J Med 373:220-31). But this combination did not provide a significant improvement in $FEV_1$ for compound heterozygous patients with only one allele of F508del.

Thus, there remains a need for additional treatments for CF, and in particular CF patients having CFTR residual function mutations.

SUMMARY

One embodiment relates to a method of treating CFTR-mediated disease in a patient, comprising administering to the patient an effective amount of a CFTR activator or a pharmaceutically acceptable salt thereof.

Another embodiment relates to a method of treating a CFTR-mediated disease in a patient, comprising administering to a patient who is receiving treatment with a CFTR potentiator and/or CFTR corrector, an effective amount of a CFTR activator or a pharmaceutically acceptable salt thereof.

Still another embodiment relates to the use of lubiprostone in the manufacture of a medicament for the treatment of CFTR-mediated diseases.

Another embodiment relates to the use of a pharmaceutical composition comprising lubiprostone in the preparation of a medicament for the treatment of CFTR-mediated diseases.

Yet another embodiment relates to lubiprostone for use in the treatment of CFTR-mediated diseases.

In one aspect of any of the above methods or uses, the patient has at least one CFTR residual function mutation.

In one aspect of any of the above methods or uses, the at least one CFTR residual function mutation is an amino acid deletion of position F508 (F508del) of wild-type CFTR amino acid sequence SEQ ID NO:1.

In still another aspect of any of the above methods or uses, the at least one CFTR residual function mutation is an amino acid deletion or substitution of wild-type CFTR amino acid sequence SEQ ID NO:1 selected from the group consisting of F508del, E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D. In still another aspect, the CFTR residual function mutation is a combination of a deletion and/or one or more substitutions of the mutations disclosed herein.

In yet another aspect of any of the above methods or uses, the patient is heterozygous for the CFTR mutation In still another aspect of any of the above methods or uses, the patient is homozygous for the CFTR mutation.

In still another aspect of any of the above methods or uses, the CFTR activator is administered as a pharmaceutical composition comprising the CFTR activator, or a pharmaceutically acceptable salt thereof.

In yet another aspect of any of the above methods or uses, the CFTR activator is lubiprostone or a pharmaceutically acceptable salt thereof.

In still another aspect of any of the above methods or uses, the methods or uses further comprise administering a pharmaceutical composition comprising at least one additional active pharmaceutical ingredient. In one aspect, the at least one additional active pharmaceutical ingredient is administered simultaneously, sequentially, in a single composition, or as one or more separate compositions. In yet another aspect, the at least one additional active pharmaceutical ingredient is a CFTR potentiator and/or CFTR corrector. In one aspect, the CFTR potentiator is selected from the group consisting of VX-770 (Ivacaftor), GLPG-1837, GLPG-2451, QBW-251, FDL-176, FDL-129, CTP-656, and PTI-P271. In yet another aspect, the CFTR corrector is selected from the group consisting of VX-809 (lumacaftor), VX-661 (tezacaftor), VX-445 (elexacaftor), VX-983, VX-152, VX-440, VX-659, GLPG-2737, P247-A, GLPG-2222, GLPG-2665, GLPG-2851, FDL-169, and PTI-C1811.

In yet another aspect of any of the above methods or uses, the patient exhibits residual CFTR activity in the apical membrane of respiratory and non-respiratory epithelia.

In still another aspect of any of the above methods or uses, the patient exhibits little to no CFTR activity in the apical membrane of respiratory epithelia.

In another aspect of any of the above methods or uses, the CFTR-mediated disease is cystic fibrosis It is to be appreciated that any feature described herein can be claimed in combination with any other feature(s) as described herein, regardless of whether the features come from the same described embodiment.

This Summary is neither intended nor should it be construed as representative of the full extent and scope of the present disclosure. Moreover, references made herein to "the present disclosure," or aspects thereof, should be understood to mean certain embodiments of the present invention and should not necessarily be construed as limiting all embodiments to a particular description. The present invention is set forth in various levels of detail in this Summary as well as in the attached drawings and the Detailed Description and no limitation as to the scope of the present invention is intended by either the inclusion or non-inclusion of elements, components, etc. in this Summary. Additional aspects of the present invention will become more readily apparent from the Detailed Description, particularly when taken together with the figures.

BRIEF DESCRIPTION OF FIGURES

FIG. 1A shows CFTR activation of Nuli-1 bronchial epithelial cells with increasing concentrations of lubiprostone (Lubi). FIG. 1B shows a comparison of CFTR activation with 20 μM forksolin/100 IBMX (F/I) and 100 nM lubiprostone (Lubi). FIG. 1C shows a comparison of CFTR activation with F/I and Lubi followed by CFTR inhibition.

FIG. 2A shows differentiated NuLi-1 cells treated with vehicle alone (Control) or lubiprostone for 24 hours prior to analysis. FIG. 1B shows changes in current after CFTR activation with 20 μM forksolin/100 μM IBMX (F/I). FIG. 1C shows quantification of sequential CFTR inhibition with 10 μM CFTR(inh)-172.

FIG. 3A shows activation of F508del/F508del CFTR genotype primary nasal epithelial cells treated with DMSO or 3 μM VX-809/100 nM VX-770 for 24 hours prior to analysis by amiloride, and either 100 nM lubiprostone (Lubi), RP-107, or forskolin/IBMX (F/I), followed by potentiation of activated CFTR with acute 1 μM VX-770. FIG. 3B shows CFTR was inhibition in these cells using 10 μM CFTR(inh)-172.

FIG. 4A shows activation after addition of amiloride and exposure to 100 nM lubiprostone (Lubi) followed by 1 μM VX-770. FIG. 4B shows inhibition of these same cells with 10 μM CFTR(inh)-172.

FIGS. 5A-5D show chronic treatment with lubiprostone alongside CFTR-modulators increases CFTR activity in CF (F505del homozygous and G551D/R117H) human nasal epithelial (HNE) cells. FIG. 5A shows representative traces of lubiprostone activation of F508del-CFTR after 24 hr treatment with the triple combination of VX-445, VX-661, and VX-770 (i.e., TRIKAFTA®) and/or lubiprostone. FIG. 5B shows chronic treatment with lubiprostone alone had no effect on F508del-CFTR activity. Treatment with VX-445/661/770 significantly increased CFTR functional capacity by approximately 10-fold. Co-treatment of lubiprostone alongside VX-445/661/770 significantly increased CFTR functional capacity above treatment with VX-445/661/770 alone by approximately 50%. Data in FIG. 5B is obtained from n=4 donors. FIG. 5C shows representative traces of lubiprostone activation of CFTR in G551D/R117H HNE after 24 hr treatment VX-770 (ivacaftor) and/or lubiprostone. FIG. 5D shows chronic treatment with lubiprostone had no effect on CFTR activity. Treatment with VX-770 significantly increased CFTR activation by approximately 30%. Co-treatment with lubiprostone alongside VX-770 significantly increased CFTR activity above treatment with VX-770 alone by approximately 30%.

DETAILED DESCRIPTION

Figure 1A:
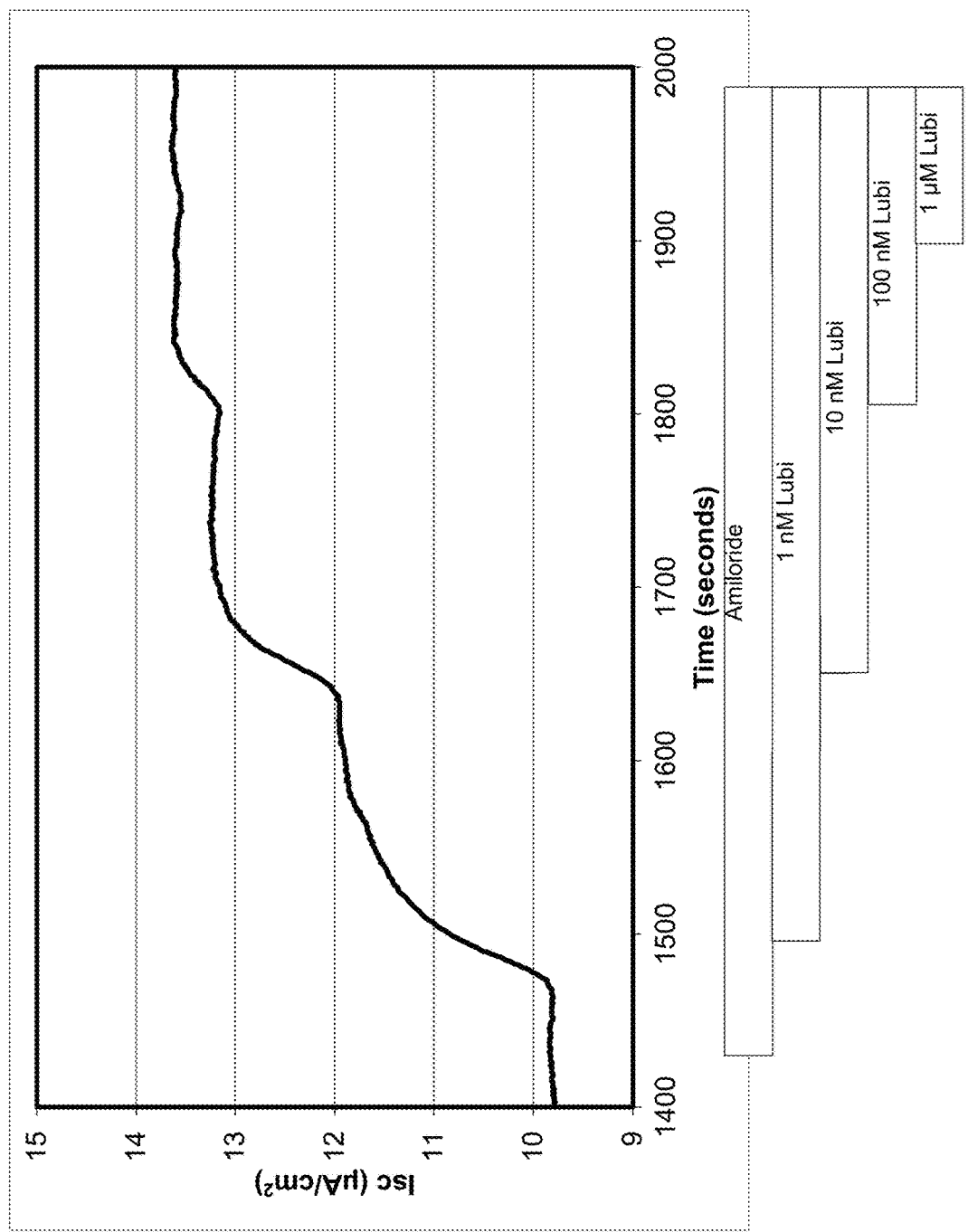
FIGS. 1A-1C show activation of normal CFTR in the NuLi-1 bronchial epithelial cell line.

This disclosure provides methods and uses for treating or reducing the severity of CFTR-mediated disorders, including CF, by administering to a subject in need thereof an effective amount of a CFTR activator, such as lubiprostone, alone or in combination with one or more secondary active agents.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. The flow of water across cellular membranes depends on tiny transepithelial osmotic gradients generated by the bulk flow of sodium and chloride, which is controlled, in part, by the CFTR anion channel.

The clinical impact of any CFTR mutation is believed to be related to the amount of total CFTR ion transport activity. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect).

Some CFTR mutations reduce CFTR protein quantity or function to such an extent that there is little to no total CFTR activity. Other mutations result only in reduced protein quantity or function at the cell surface which can produce partial CFTR activity. These mutations are called residual function mutations. For example, some CFTR mutations that cause defective mRNA splicing, such E831X, result in reduced protein synthesis, but deliver some functional CFTR to the surface of the cell to provide residual function. Other CFTR mutations that reduce conductance and/or gating, such as R117H, result in a normal quantity of CFTR channels at the surface of the cell, but the functional level is low, resulting in residual function. Some mutations, such as F508del, result in multiple CFTR protein defects.

Both CFTR alleles play a role in determining phenotype of disease severity. Common residual function mutations include F508del, E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D (wild-type CFTR amino acid sequence is represented by SEQ ID NO:1). In these methods and/or uses, the CFTR mutation may be F508del. Patients with residual function mutations may experience the symptoms of CFTR-mediated diseases later in life and symptoms may be less severe than in patients with other mutations. Patients with CFTR residual function mutations tend to have higher rates of pancreatic sufficiency, less elevated sweat chloride levels, and less severe pulmonary disease than patients with other mutations. However, patients with a residual function mutation generally have progressive lung function decline and other complications of CF that may still lead to a severe disease stage and cause premature death. The life expectancy and quality of life for CFTR residual function mutation patients is well below that of persons without CF.

Activation of CFTR in vitro is commonly performed using molecules that directly increase intracellular cAMP levels, thereby stimulating CFTR-mediated chloride transport. While these molecules are not suitable for use therapeutically, an FDA-approved compound that activates CFTR through this same mechanism, the $\beta_2$ adrenergic receptor agonist albuterol, was recently tested for its ability to activate F508del CFTR that has been corrected and potentiated (PMID 29467332). Unfortunately, the results of this study indicated that chronic treatment with albuterol decreased the function of both non-CF CFTR and corrected/potentiated F508del CFTR.

The current inventors have surprisingly discovered that alternative CFTR activators can be used chronically to activate non-CF CFTR and corrected/potentiated F508del CFTR. For example, as demonstrated herein, lubiprostone demonstrated the potent ability to acutely activate both non-CF and F508del CFTR. When cells obtained from non-CF individuals were treated long-term with lubiprostone, it did not result in a decrease CFTR function. Chronic lubiprostone exposure also did not abrogate the effects of the FDA-approved CFTR corrector VX-809 and potentiator VX-770 upon cells obtained from individuals with CF harboring two copies of F508del CFTR. Surprisingly, this chronic exposure to lubiprostone enhanced the chloride transporting ability of corrected/potentiated F508del CFTR.

This disclosure provides methods and/or uses of treating a CFTR-mediated disease such as CF in patients with residual function mutations, and/or chemically modulated CFTR, by administering activators of CFTR, or pharmaceutical compositions containing CFTR activators, to these patients.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene. Examples of CFTR mutations include F508del, E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D. An exemplary CFTR mutation is the F508del mutation.

A "residual function mutation" as used herein, refers to a mutation in the CFTR gene that results in reduced CFTR protein quantity or function of the protein at the cell surface. Non-limiting examples of CFTR gene mutations known to result in a residual function phenotype include E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D. As provided for herein, amino acid deletions and/or substitutions in regard to the CFTR gene are in relation to the wild-type amino acid sequence represented by SEQ ID NO:1. Further, the CFTR residual function mutation can be a combination of a deletion and/or one or more substitutions of the mutations disclosed herein.

Residual Function in CF is determined clinically based on population characteristics such as lower sweat chloride levels and incidence of pancreatic sufficiency. Residual function may be indicative of the presence of a CFTR mutation that results in some functional CFTR protein at the cell surface leading to residual CFTR ion transport activity.

Residual CFTR function can be characterized at the cellular (in vitro) level using cell-based assays, such as an FRT assay (Van Goor, et al., (2009) PNAS 106(44); 18825-30; and Van Goor, et al. (2011) PNAS 108(46):18843-46) to measure the amount of chloride transport through the mutated CFTR channels. Residual function mutations result in a reduction but not complete elimination of CFTR-dependent ion transport. For example, residual function mutations may result in at least about 10%, about 20%, about 30%, about 40%, about 50%, about 60%, about 70%, about 80% or about 90% reduction of CFTR activity in the FRT assay. In another example, the residual function mutation may result in up to about 90% reduction in CFTR activity in the FRT assay.

Subjects and/or patients with residual function may have variable disease with some subjects showing a delayed decline in lung function or age of diagnosis compared to patients with more serious CFTR mutations, such as subjects homozygous for the F508del mutation.

Subjects and/or patients carrying residual function CFTR mutations may demonstrate variability in their clinical phenotype, which may include delayed disease progression, chronic pulmonary disease, pulmonary exacerbations, increasing frequency of hospitalizations over the course of their lifespan, and/or markedly reduced median life expectancy compared with the general population. The treatment methods and/or uses of this disclosure may improve or resolve any one or more of these phenotypes.

As provided for herein, diseases and/or conditions that can be treated by the methods and/or uses disclosed herein include CF, asthma, bronchiectasis, chronic obstructive pulmonary disease (COPD), constipation, Diabetes mellitus, dry eye disease, pancreatitis, rhinosinusitis, Sjogren's Syndrome, and other CFTR-mediated diseases. In a preferred aspect, the disease is CF.

As used herein, a subject and/or patient who is "homozygous" for a particular gene mutation has the same mutation on each allele. The term "heterozygous" as used herein, refers to a subject having a particular gene mutation on one allele, and a different mutation or no mutation on the other allele. Subjects that may benefit from the methods of treatment of the invention and from pharmaceutical compositions described herein for use in treating CFTR-mediated diseases include patients who have homozygous or heterozygous mutations on the CFTR gene, but also have a residual function phenotype.

As used herein, the term "modulator" refers to a compound that alters or increases the activity of a biological compound such as a protein. For example, a CFTR modulator is a compound that generally increases the activity of CFTR. The increase in activity resulting from a CFTR modulator includes but is not limited to compounds that correct, potentiate, stabilize and/or amplify CFTR.

As used herein, a "CFTR activator" is a compound that acts on its own to stimulate CFTR-mediated ion transport, and includes agents that increase cAMP levels, such as b-adrenergic agonists, adenylate cyclase activators, and phosphodiesterase inhibitors. Exemplary CFTR activators include prosotones (such as lubiprostone, unoprostone, or cobiprostone), forskolin, isobutylmethylxanthine (IBMX), beta-2-agonists (such as albuterol and/or isoproterenol), genistein, pyrrolo[2,3-b]pyrazines derivatives (such as RP-107), 4-chlorobenzo[F]isoquinoline (CBIQ), 2-thioxo-4-amino-thiazoles (such as A01 and A02), 5-((Z)-2-(2-(Allyloxy)phenyl)-1-cyanovinyl)-3-amino-1H-pyrazole-4-carbonitrile (Cact-A1).

As used herein, a "CFTR corrector" is a compound that acts by increasing the delivery and amount of functional CFTR protein to the cell surface, resulting in enhanced ion transport.

As used herein, a "CFTR potentiator" is a compound that act in the presence of endogenous or pharmacological CFTR activators to increase the channel gating activity of cell-surface localized CFTR, resulting in enhanced ion transport.

Depending on the molecular consequence of the mutation and disease severity, CFTR activators, potentiators, and correctors may be co-administered to maximize clinical efficacy or therapeutic window, if needed.

As used herein, the term "active pharmaceutical ingredient" or "API" refers to a biologically active compound.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e., exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). As used herein, the term "polymorphous" refers to a solid material that may exist in two or more amorphous forms. The different amorphous forms may have similar or disparate stabilities under storage and/or administration conditions.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). A solid dispersion may include the polymer constituting the dispersed phase, and the drug constitute the continuous phase. Or, a solid dispersion includes the drug constituting the dispersed phase, and the polymer constituting the continuous phase.

The term "patient" or "subject" is used interchangeably and refers to a mammal, including humans.

The terms "effective dose" or "effective amount" are used interchangeably herein and refer to that amount of a compound that produces the desired effect for which it is administered (e.g., the treatment of a CFTR-mediated disease such as CF, improvement in a CFTR-mediated disease such as CF or a symptom of a CFTR-mediated disease such as CF, or reducing the severity of a CFTR-mediated disease such as CF or a symptom of a CFTR-mediated disease such as CF). The exact amount of an effective dose will depend on the purpose of the treatment, and the patient, and will be ascertainable by one skilled in the art using known techniques.

As used herein, the terms "treatment," "treating," and the like generally mean treatments resulting in the improvement of a CFTR-mediated disease such as CF or its symptoms or lessening the severity of a CFTR-mediated disease such as CF or its symptoms in a subject. As used herein, "treatment" of a subject having a CFTR-mediated disease, such as CF, includes, but is not limited to: increased growth of the subject, increased weight gain, reduction of mucus in the lungs, improved pancreatic and, or liver function, reduction of chest infections, increase in $FEV_1$ (forced expiratory volume in one second), decreases in sweat chloride, reductions in exacerbations, increased life span, decreased progression of disease, and/or reductions in coughing or shortness of breath. Improvements in or lessening the severity of any of these symptoms can be readily assessed according to standard methods and techniques known in the art.

As used herein, the term "in combination with" when referring to two or more compounds, agents, or additional active pharmaceutical ingredients, means the administration of two or more compounds, agents, or active pharmaceutical ingredients to the patient prior to, concurrent with, or subsequent to each other. The terms "about" and "approximately," when used in connection with doses, amounts, or weight percent of ingredients of a composition or a dosage form, include the value of a specified dose, amount, or weight percent, or a range of the dose, amount, or weight percent that is recognized by one of ordinary skill in the art to provide a pharmacological effect equivalent to that obtained from the specified dose, amount, or weight percent. For example, reference to "about" and "approximately" typically includes the value of a specified dose, amount, or weight percent, or a range of the dose, amount, or weight percent±10%.

Lubiprostone is 7-[(1R,3R,6R,7R)-3-(1,1-difluoropentyl)-3-hydroxy-8-oxo-2-oxabicyclo[4.3.-0]non-7-yl]heptanoic acid, a bicyclic 13,14-dihydro-15-keto-16,16-difluoro-prostaglandin E1 derivative with the prostanoic acid backbone which is a C20 fatty acid. Lubiprostone is the active pharmaceutical ingredient (API) in the drug product AMITIZA®, a gastrointestinal agent marketed by Sucampo Pharmaceuticals, Inc. and approved by the United States Food and Drug Administration (FDA) for the treatment of Chronic Idiopathic Constipation in adults, and the treatment of Irritable Bowel Syndrome with constipation (ISB-C) in adult women aged 18 and over. Reference to lubiprostone in this disclosure includes this compound as well as the known polymorphic forms, as described in US Patent Publication No. 2013/0096325, which is incorporated herein by this reference. As noted above, lubiprostone is available commercially. Lubiprostone and pharmaceutically acceptable salts thereof may be synthesized as described in any one of US Patent Publications No. 2015/0005528; 2013/0225842; 2013/0184476; 2013/0096325; 2012/0309990; 2012/0270931; 2012/0065409; and 2011/0028541; each of which is incorporated herein by reference.

In the methods and/or uses of this disclosure, lubiprostone may have one or more isotopically enriched atoms. For example, one or more hydrogens in the chemical compound may optionally be replaced by deuterium or tritium, or one or more carbon atoms may optionally be replaced by $^{13}C$- or $^{14}C$-enriched carbon. Such compounds may be useful as analytical tools or probes in biological assays, or as therapeutic agents. Deuterated analogs of lubiprostone are disclosed in US Patent Publications No. 2009/0082442, incorporated herein by reference.

As used herein, a "pharmaceutically acceptable salt" refers to any salt or salt of an ester of a compound of this disclosure that, upon administration to a recipient, is capable of providing, either directly or indirectly, a compound of this disclosure. Pharmaceutically acceptable salts are well known in the art. For example, pharmaceutically acceptable salts may include the FDA-Approved Commercially Marketed Salts: Acetate, Aluminum, Benzenesulfonate, Benzathine, Benzoate, Bicarbonate, Bitartrate, Bromide, Calcium, Calcium edetate, Camsylate, Carbonate, Chloride, Choline, Citrate, Diethanolamine, Dihydrochloride, Edetate, Edisylate, Estolate, Esylate, Ethylenediamine, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Lithium, Magnesium, Malate, Maleate, Mandelate, Meglumine, Mesylate, Methylbromide, Methylnitrate, Methylsulfate, Mucate, Napsylate, Nitrate, Pamoate (Embonate), Pantothenate, Phosphate/diphosphate, Polygalacturonate, Potassium, Potassium Salicylate, Sodium, Stearate, Subacetate, Succinate, Sulfate, Tannate, Tartrate, Teociate, Triethiodide, and Zinc.

Pharmaceutically acceptable salts may include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}$ alkyl$)_4$ salts. Exemplary alkali or alkaline earth metal salts include sodium, lithium, potassium, calcium, magnesium, and the like. Further pharmaceutically acceptable salts include, when appropriate, ammonium, quaternary ammonium, and amine cations formed using counterions such as halide, hydroxide, carboxylate, sulfate, phosphate, nitrate, lower alkyl sulfonate and aryl sulfonate. Other representative pharmaceutically acceptable salts include besylate and glucosamine salts.

Pharmaceutical Compositions

Pharmaceutical compositions for use in the methods of this disclosure may comprise, in addition to a CFTR activator, such as lubiprostone, a pharmaceutically acceptable salt of any of the foregoing, one or more of a vehicle, adjuvant, or carrier, such as a filler, a disintegrant, a surfactant, a binder, a lubricant, or combinations thereof.

Compositions comprising lubiprostone are described in US Patent Publication No. 2012/0270931, which is incorporated herein by this reference.

The methods and/or uses of this disclosure may include the use of a pharmaceutical composition comprising a CFTR activator, such as lubiprostone, or a pharmaceutically acceptable salt thereof, and a pharmaceutically acceptable carrier.

A pharmaceutical composition used in these methods may, in addition to the CFTR activator, comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York disclose various carriers used in formulating pharmaceutically acceptable compositions and known techniques for the preparation thereof Except insofar as any conventional carrier medium is incompatible with the CFTR activator compounds, such as by producing any undesirable biological effect or otherwise interacting in a deleterious manner with any other component(s) of the pharmaceutically acceptable composition, its use is contemplated to be within the scope of this disclosure. Some examples of materials which can serve as pharmaceutically acceptable carriers include, but are not limited to, ion exchangers, alumina, aluminum stearate, lecithin, serum proteins such as human serum albumin, buffer substances such as phosphates, glycine, sorbic acid, or potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate, powdered tragacanth, malt, gelatin, talc, excipients such as cocoa butter and suppository waxes, oils such as peanut oil, cottonseed oil, safflower oil, sesame oil, olive oil, corn oil and soybean oil, glycols such as propylene glycol or polyethylene glycol, esters such as ethyl oleate and ethyl laurate, agar, buffering agents such as magnesium hydroxide and aluminum hydroxide, alginic acid, pyrogen-free water, isotonic saline, Ringer's solution, ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of the formulator of the pharmaceutical composition.

Methods of Treatment/Use of CFTR Activator Compounds for Treatment

This disclosure provides methods of treating a CFTR-mediated disease in a patient with a CFTR residual function mutation, and/or chemically modulated CFTR, by administering a CFTR activator compound to the patient. Further, this disclosure provides for the use of a CFTR activator compound in the manufacture of a medicament for the treatment of CFTR-mediated diseases including those caused by a CFTR residual function mutation and/or a chemically modulated CFTR. Still further, this disclosure provides for the use of a pharmaceutical composition comprising a CFTR activator in the preparation of a medicament for the treatment of CFTR-mediated diseases including those caused by a CFTR residual function mutation and/or a chemically modulated CFTR. Yet further, this disclosure provides for a CFTR activator for use in the treatment of CFTR-mediated diseases including those caused by a CFTR residual function mutation and/or a chemically modulated CFTR.

In these methods and/or uses, the residual function mutation may result in the patient suffering from CF, or symptoms thereof. In these methods, the CFTR activator, or a pharmaceutically acceptable salt thereof, may be administered in combination with another therapeutic agent effective for the treatment of CFTR-mediated diseases, such as CF, as separate compositions or in a single composition.

Thus, methods and/or uses of this disclosure may include treating CFTR-mediated disease in a patient with a CFTR residual function mutation by administering a pharmaceutical composition comprising a CFTR activator, such as lubiprostone, or a pharmaceutically acceptable salt thereof, which may include a pharmaceutically acceptable carrier. These methods may include the simultaneous or sequential administration of a pharmaceutical composition comprising another therapeutic agent effective for the treatment of CFTR-mediated diseases, which may include a pharmaceutically acceptable carrier.

In these methods and/or uses of administering a CFTR activator, the patient to whom the CFTR activator is administered may be receiving treatment with a CFTR potentiator and/or CFTR corrector. In these methods, the CFTR activator, such as lubiprostone, or a pharmaceutically acceptable salt thereof, is synergistic in effect with the CFTR potentiator and/or CFTR corrector in treating the CFTR-mediated disease, such as cystic fibrosis. The CFTR potentiator that the patient is receiving may be one or more of VX-770 (Ivacaftor), GLPG-1837, GLPG-2451, QBW-251, FDL-176, FDL-129, CTP-656, and PTI-P271. The CFTR corrector that the patient is receiving may be one or more of VX-809 (lumacaftor), VX-661 (tezacaftor), VX-445 (elexacaftor), VX-983, VX-152, VX-440, VX-659, GLPG-2737, P247-A, GLPG-2222, GLPG-2665, GLPG-2851, FDL-169, and PTI-C1811.

The methods of this disclosure include methods of treating or reducing the severity of a CFTR-mediated disease such as CF in a patient, comprising administering to the patient an effective amount of a lubiprostone or a pharmaceutically acceptable salt thereof. These methods include use of lubiprostone in the manufacture of a medicament for the treatment of CFTR-mediated diseases, such as CF. These methods also include use of a pharmaceutical composition comprising lubiprostone in the preparation of a medicament for the treatment of CFTR-mediated diseases, such as CF. These methods also include lubiprostone for use in the treatment of CFTR-mediated diseases, such as CF.

In these methods and/or uses, the CFTR residual function mutation may be any one or more of the CFTR mutations selected from F508del, E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D. In these methods and/or uses, the CFTR mutation may be a F508del mutation.

In these methods and/or uses, the patient may be heterozygous for at least one residual function mutation on one allele and a second CFTR gene mutation on the other allele. For example, the patient may be heterozygous for a F508del mutation on one other allele and another CFTR mutation on another allele. Alternatively, the patient may be heterozygous for a F508del mutation on one other allele and wild type (i.e. no CFTR mutation) on another allele. Alternatively, the patient may be homozygous for the F508del mutation on the CFTR gene.

In the methods and/or uses of this disclosure, modulating a CFTR-mediated disease, particularly CF, in a patient with a residual function mutation, will typically involve a combination therapy. For example, a composition comprising lubiprostone or a pharmaceutically acceptable salt thereof may be administered concurrently with, prior to, or subsequent to a composition comprising another therapeutic agent useful in the treatment of CFTR-mediated diseases. These additional therapeutic agents may include additional CFTR activators, and/or CFTR potentiators, and/or CFTR correctors.

The methods and/or uses of this disclosure are useful for treating, reducing the severity of, or symptomatically treating a CFTR-mediated disease such as CF in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary concentrations, or ex vivo biochemical or histochemical techniques to monitor cell surface density of CFTR protein. Using such methods, residual CFTR activity can be readily detected in patients heterozygous or homozygous for a variety of different mutations, including patients homozygous or heterozygous for the most common mutation, F508del. These methods of this disclosure are also useful for treating, reducing the severity of, or symptomatically treating cystic fibrosis in patients who exhibit residual CFTR activity. The methods of this disclosure are also useful for treating, lessening the severity of, or symptomatically treating cystic fibrosis in patients who exhibit little to no residual CFTR activity in the apical membrane of respiratory epithelia.

The amount of CFTR activator compound, such as lubiprostone, or pharmaceutically acceptable salts thereof, or pharmaceutical composition(s) comprising the CFTR activator(s) administered in the methods of this disclosure will vary from subject to subject, depending on the species, age, and general condition of the subject, the severity of the CFTR-mediated disease, the particular agent, its mode of administration, and the like. Pharmaceutical compositions comprising the CFTR activator may be formulated in dosage unit form for ease of administration and uniformity of dosage. The expression "dosage unit form" as used herein refers to a physically discrete unit of agent appropriate for the patient to be treated. It will be understood, however, that the total daily usage of the CFTR activator compounds and compositions of this disclosure will be decided by the medical professional within the scope of sound medical judgment. The specific effective dose level for any particular patient or subject will depend upon a variety of factors including the disorder being treated and the severity of the disorder; the activity of the specific compound employed; the specific composition employed; the age, body weight, general health, genetic profile, sex, and diet of the patient; the time of administration, route of administration, and rate of excretion of the specific CFTR activator compound employed; the duration of the treatment; drugs used in combination or coincidental with the specific compound employed, and like factors well known in the medical arts.

The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

Numerical ranges recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

As used herein, the term "about" is synonymous with the term "approximately." Illustratively, the use of the term "about" indicates that a value includes values slightly outside the cited values. Variation may be due to conditions such as experimental error, manufacturing tolerances, variations in equilibrium conditions, and the like. In some embodiments, the term "about" includes the cited value plus or minus 10%. In all cases, where the term "about" has been used to describe a value, it should be appreciated that this disclosure also supports the exact value.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The described features, structures, or characteristics of the methods, compositions, and kits provided herein may be combined in any suitable manner in one or more embodiments. In the description, numerous specific details are provided, to provide a thorough understanding of embodiments. One skilled in the relevant art will recognize, however, that the embodiments may be practiced without one or more of the specific details, or with other methods, components, materials, and so forth. In other instances, well-known structures, materials, or operations are not shown or described in detail to avoid obscuring aspects of the embodiments.

The contents of all references, patents and published patent applications cited throughout this Application, as well as their associated figures are hereby incorporated by reference in their entirety. In case of conflict, the present specification, including its specific definitions, will control.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

EXAMPLES

Example 1

Lubiprostone Activates Normal CFTR in Bronchial Epithelial Cells.

Figures 1B, 1C:
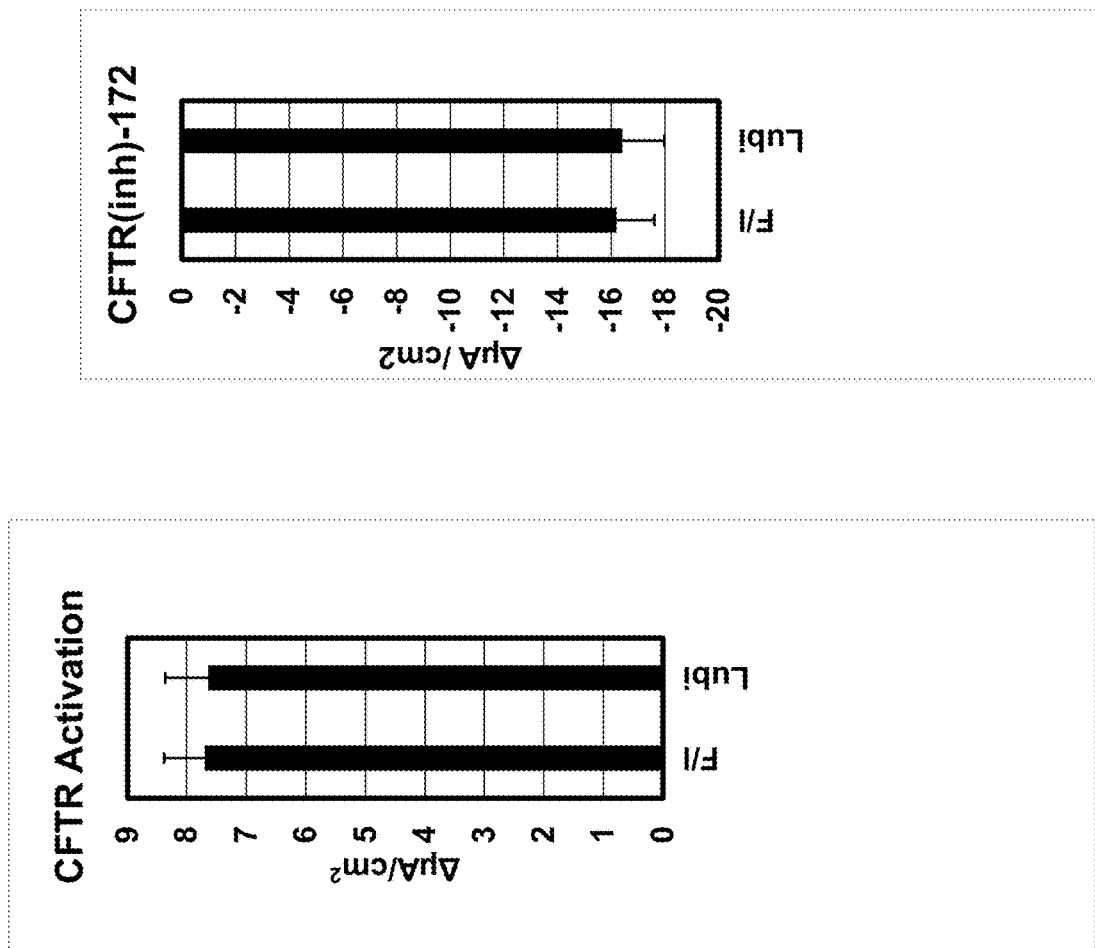

This example demonstrates that lubiprostone maximally activates normal CFTR in the NuLi-1 bronchial epithelial cell line. NuLi-1 cells were differentiated at the air-liquid interface for 3 weeks, then sequentially treated with increasing concentrations of lubiprostone (Lubi) to the apical surface (FIG. 1A) in an Ussing chamber; maximum CFTR activation was achieved at a concentration of 100 nM. CFTR activation with 20 µM forskolin/100 µM IBMX (F/I) and 100 nM lubiprostone (Lubi) were compared (FIG. 1B), followed by CFTR inhibition (FIG. 1C).

Example 2

Chronic Lubiprostone Exposure Increases Functional Capacity of Bronchial Epithelial Cells.

Figure 2A:
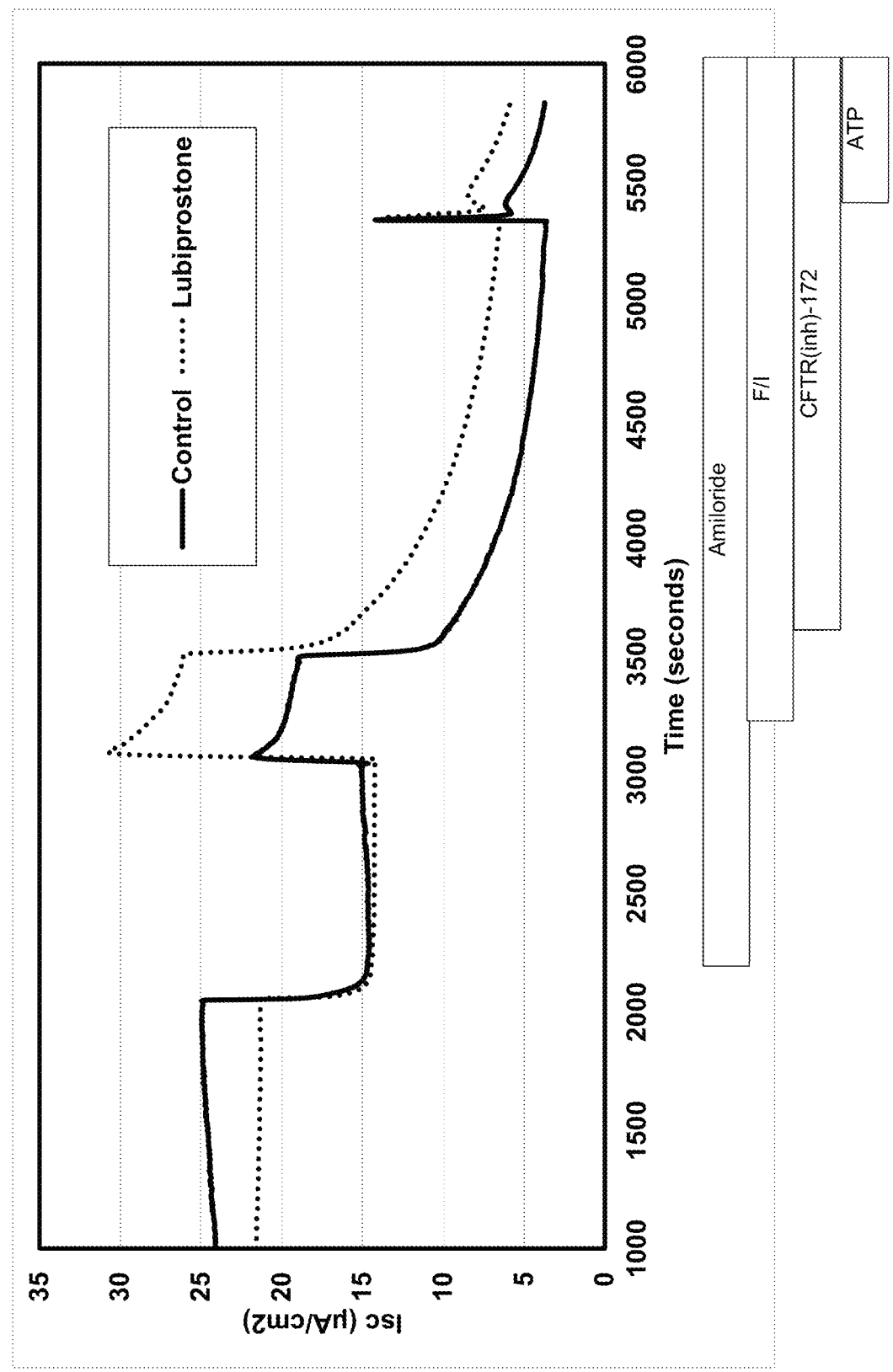
FIGS. 2A-2C show functional capacity of normal CFTR in NuLi-1 bronchial epithelial cells during chronic lubiprostone exposure.
Figure 2C:
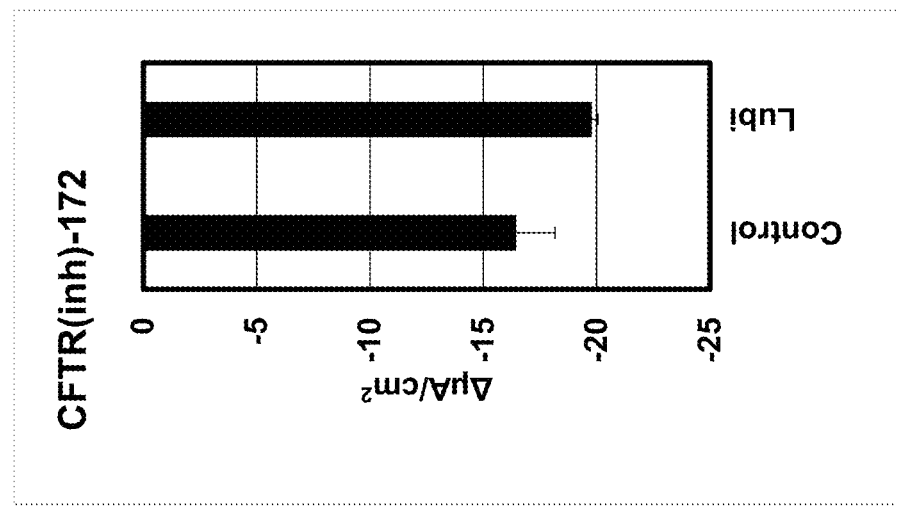
Figure 2B:
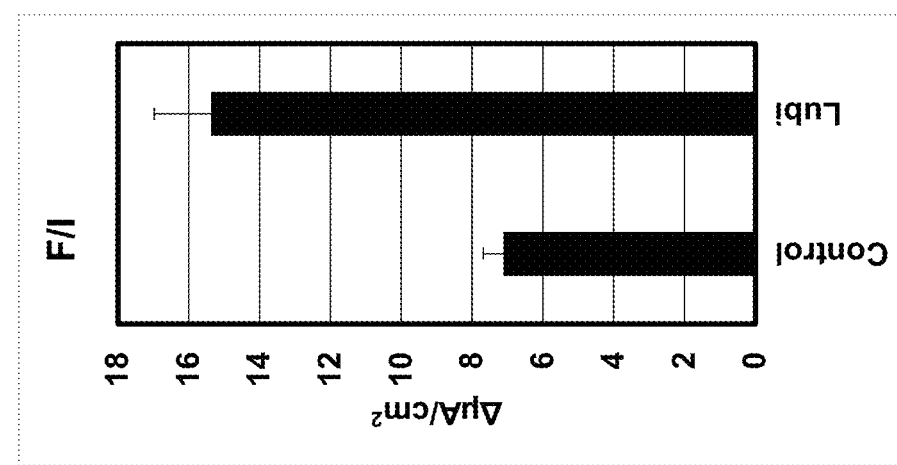

This example demonstrates that chronic lubiprostone exposure increases the functional capacity of normal CFTR in NuLi-1 bronchial epithelial cell line. Differentiated NuLi-1 cells were treated with vehicle alone (Control) or 100 nM lubiprostone for 24 hours prior to analysis in an Ussing chamber. FIG. 1A shows the treatment timeline. FIG. 1B shows the changes in the current after CFTR activation with 20 µM forkskolin/100 µM IBMX (F/I), and FIG. 2B shows the quantification of the sequential CFTR inhibition with 10 µM CFTR(inh)-172.

Example 3

Lubiprostone Maximally Activates F508del CFTR in Primary Nasal Epithelial Cells.

Figure 3B:
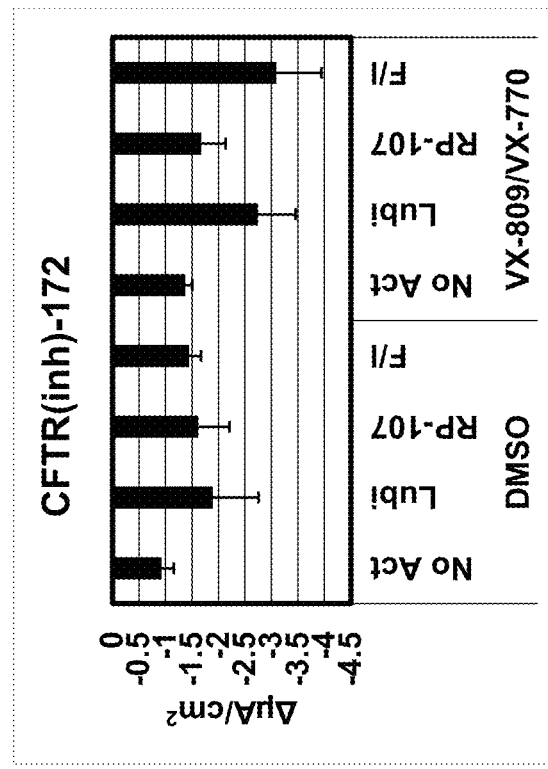
FIGS. 3A and 3B show activation of F508del CFTR in uncorrected and corrected F508del/F508del CFTR primary nasal epithelial cells.
Figure 3A:
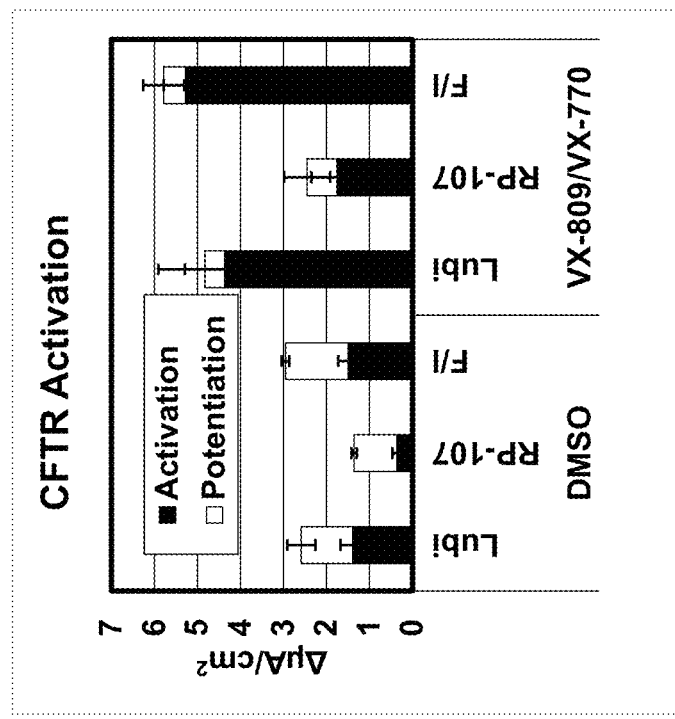

This example demonstrated that lubipostone maximally activates F508del CFTR in uncorrected and corrected F508del/F508del CFTR primary nasal epithelial cells. Primary nasal epithelial cells obtained from an individual with CF harboring the homozygous F508del/F508del CFTR genotype were treated with DMSO or 3 µM VX-809(lumacaftor)/100 nM VX-770 (ivacaftor) for 24 hours prior to analysis in an Ussing chamber. After addition of amiloride, CFTR was activated by exposure to either 100 nM lubiprostone (Lubi), RP-107, or forskolin/IBMX (F/I), followed by potentiation of activated CFTR with acute 1 µM VX-770. FIG. 3A shows the activation of the F508del CFTR by these treatments, alone or in combination with VX-809 and VX-770. FIG. 3B shows the inhibition of the F508del CFTR using 10 µM CFTR(inh)-172.

Example 4

Lubiprostone Activates F508del CFTR in Chronically Treated Primary Nasal Epithelial Cells.

Figure 4B:
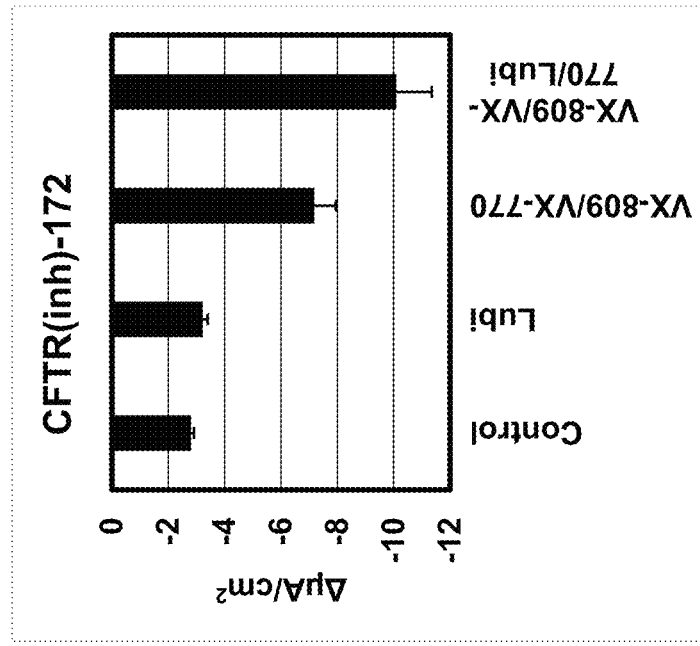
FIGS. 4A and 4B show activation and inhibition of F508del CFTR in primary nasal epithelial cells with DMSO, 100 nM lubiprostone, 3 μM VX-809/100 nM VX-770, or VX-809/VX-770/Lubiprostone for 24 hours prior to analysis.
Figure 4A:
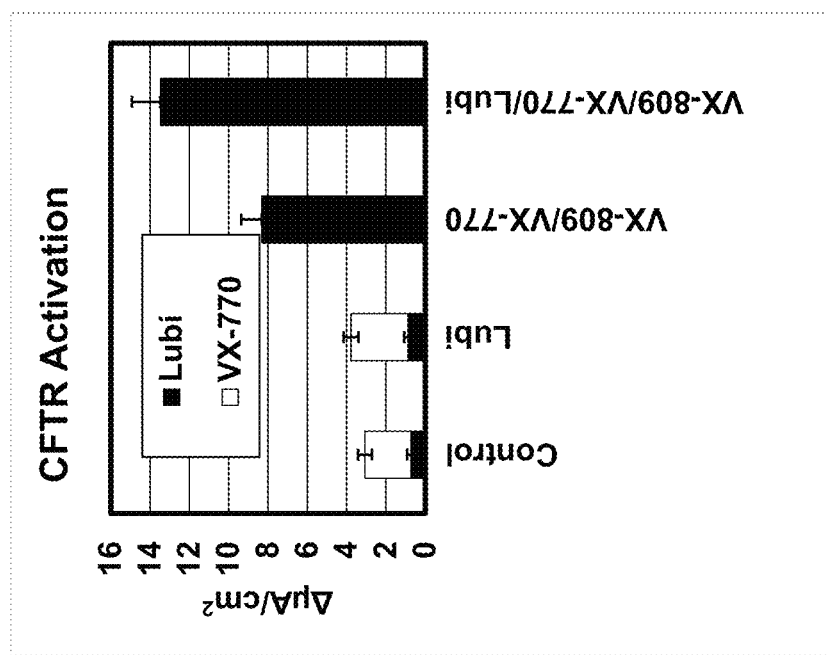

This example demonstrates that chronic treatment with lubiprostone is able to activate F508del CFTR. Nasal epithelial cells obtained from an individual with CF harboring the F508del/F508del CFTR genotype were treated with DMSO, 100 nM lubiprostone, 3 µM VX-809/100 nM VX-770, or VX-809/VX-770/Lubiprostone for 24 hours prior to analysis in an Ussing chamber. After the addition of amiloride, CFTR was activated by exposure to 100 nM lubiprostone (Lubi) followed by 1 µM VX-770. FIG. 4A shows the activation of these cells. Activation of these cells was followed by inhibition of CFTR with 10 µM CFTR (inh)-172 and FIG. 4B shows the inhibition in these cells.

Example 5

Lubiprostone with CFTR-Modulators Increases F505del CFTR Activity in CF Primary Human Nasal Epithelial (HNE) Cells.

This example demonstrates that chronic treatment with lubiprostone alongside CFTR-modulators increases CFTR activity in CF (F505del homozygous and G551D/R117H) HNE cells. Primary HNE cells were obtained from non-CF and CF individuals by nasal brushing. HNE cells were raised at an air-liquid interface for 21-28 days on collagen-coated 0.33 µm diameter cell culture inserts (Costar SNAP-WELL™, Corning) at 37° C. HNE monolayers were assayed in Ussing chambers with identical Ringer's solutions in both the apical and basolateral sides (i.e., symmetrical chloride) with a voltage clamp applied (mV=0). After 21 days in ALI, both CF and non-CF monolayers have suitable baseline transepithelial electric resistance (>200 S2 $cm^{-2}$) and baseline transepithelial potential difference (−5 to −10 mV), visibly apparent beating ciliated cells, and quick responsiveness ($\Delta I_{sc}$) to classic electrophysiological pharmacological compounds. Acute test compounds applied: amiloride (100 µM; apical), forskolin (20 µM; Fsk) and 3-Isobutyl-1-methylxanthine (100 µM; IBMX) (Fsk/IBMX; apical and basolateral), lubiprostone (100 nM; apical and basolateral), CFTRinh-172 (10 µM; apical), ATP (100 µM; apical).

The results are provided for in FIGS. 5A-5D. FIG. 5A shows representative traces of lubiprostone activation of F508del-CFTR after 24 hr treatment with the triple combination of VX-445, VX-661, and VX-770 (i.e., TRIKAFTA®) and/or lubiprostone. FIG. 5B shows chronic treatment with lubiprostone alone had no effect on F508del-CFTR activity. Treatment with VX-445/661/770 significantly increased CFTR functional capacity by approximately 10-fold. Co-treatment of lubiprostone alongside VX-445/661/770 significantly increased CFTR functional capacity above treatment with VX-445/661/770 alone by approximately 50%. Data in FIG. 5B is obtained from n=4 donors. FIG. 5C shows representative traces of lubiprostone activation of CFTR in G551D/R117H HNE after 24 hr treatment VX-770 (ivacaftor) and/or lubiprostone. FIG. 5D shows chronic treatment with lubiprostone had no effect on CFTR activity. Treatment with VX-770 significantly increased CFTR activation by approximately 30%. Co-treatment with lubiprostone alongside VX-770 significantly increased CFTR activity above treatment with VX-770 alone by approximately 30%.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A method of treating a cystic fibrosis transmembrane conductance regulator (CFTR)-mediated disease in a human patient, comprising administering to the patient an effective amount of a CFTR activator or a pharmaceutically acceptable salt thereof, and an effective amount of a CFTR potentiator and/or at least one CFTR corrector; wherein the CFTR activator is lubiprostone or a pharmaceutically acceptable salt thereof, the CFTR potentiator is VX-770 (Ivacaftor), and wherein the CFTR corrector is selected from the group consisting of VX-809 (lumacaftor), VX-661 (tezacaftor), VX-445 (elexacaftor) and combinations thereof.

2. The method of claim 1, wherein the patient has at least one CFTR residual function mutation.

3. The method of claim 1, wherein the patient has at least one CFTR-mutation, wherein the mutation is an amino acid deletion of position F508 (F508del) of wild-type CFTR amino acid sequence SEQ ID NO:1.

4. The method of claim 2, wherein the at least one residual function mutation is an amino acid substitution of wild-type CFTR amino acid sequence SEQ ID NO:1 selected from the group consisting of E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D.

5. The method according to claim 3, wherein the patient is heterozygous for the CFTR mutation.

6. The method according to claim 3, wherein the patient is homozygous for the CFTR mutation.

7. The method of claim 1, wherein the CFTR activator is administered as a pharmaceutical composition comprising the CFTR activator, or a pharmaceutically acceptable salt thereof.

8. The method according to claim 1, further comprising administering a pharmaceutical composition comprising at least one additional active pharmaceutical ingredient.

9. The method according to claim 1, wherein the at least one CFTR potentiator and/or the at least one CFTR corrector is administered simultaneously, sequentially, in a single composition, or as one or more separate compositions.

10. The method of claim 1, wherein the patient exhibits residual CFTR activity in the apical membrane of respiratory and non-respiratory epithelia.

11. The method of claim 1, wherein the patient exhibits little to no CFTR activity in the apical membrane of respiratory epithelia.

12. The method of claim 1, wherein the CFTR-mediated disease is cystic fibrosis.

13. A method of treating a cystic fibrosis transmembrane conductance regulator (CFTR)-mediated disease in a human patient, comprising administering to a human patient who is receiving treatment with a CFTR potentiator and/or CFTR corrector, an effective amount of a CFTR activator or a pharmaceutically acceptable salt thereof, wherein the CFTR activator is lubiprostone or a pharmaceutically acceptable salt thereof, the CFTR potentiator is VX-770 (Ivacaftor), and wherein the CFTR corrector is selected from the group consisting of VX-809 (lumacaftor), VX-661 (tezacaftor), VX-445 (elexacaftor) and combinations thereof.

14. The method of claim 13, wherein the patient has at least one CFTR residual function mutation.

15. The method of claim 13, wherein the patient has at least one CFTR mutation, wherein the mutation is an amino acid deletion of position F508 (F508del) of wild-type CFTR amino acid sequence SEQ ID NO:1.

16. The method of claim 14, wherein the at least one CFTR residual function mutation is an amino acid substitution of wild-type CFTR amino acid sequence SEQ ID NO:1 selected from the group consisting of E56K, P67L, R74W, D110E, D110H, R117C, R117H, G178R, E193K, L206W, R347H, R352Q, A455E, S549N, S549R, G551D, G551S, D579G, S945L, S977F, F1052V, K1060T, A1067T, R1070W, F1074L, D1152H, G1244E, S1251N, S1255P, D1270N, and G1349D.

17. The method of claim 15, wherein the patient is heterozygous for the CFTR mutation.

18. The method of claim 15, wherein the patient is homozygous for the CFTR mutation.

19. The method of claim 13, wherein the CFTR activator is administered as a pharmaceutical composition comprising the CFTR activator, or a pharmaceutically acceptable salt thereof.

20. The method of claim 13, wherein the patient exhibits residual CFTR activity in the apical membrane of respiratory and non-respiratory epithelia.

21. The method of claim 13, wherein the patient exhibits little to no CFTR activity in the apical membrane of respiratory epithelia.

22. The method of claim 13, wherein the CFTR-mediated disease is cystic fibrosis.

* * * * *

UNITED STATES PATENT AND TRADEMARK OFFICE
CERTIFICATE OF CORRECTION

| | |
|---|---|
| PATENT NO. | : 11,963,965 B2 |
| APPLICATION NO. | : 17/130580 |
| DATED | : April 23, 2024 |
| INVENTOR(S) | : Preston E. Bratcher and Pamela L. Zeitlin |

It is certified that error appears in the above-identified patent and that said Letters Patent is hereby corrected as shown below:

In the Claims

In Claim 9, Column 25, Lines 51-52 please delete "The method according to claim 1, wherein the at least one CFTR potentiator and/or the at least one CFTR corrector" and insert --The method according to claim 1, wherein the CFTR potentiator and/or the at least one CFTR corrector--

Signed and Sealed this
Second Day of July, 2024

Katherine Kelly Vidal
*Director of the United States Patent and Trademark Office*